US011826743B2

(12) United States Patent
Wu et al.

(10) Patent No.: US 11,826,743 B2
(45) Date of Patent: Nov. 28, 2023

(54) HALOGEN-CONTAINING COMPOUND AND USE THEREOF AS CATALYST LIGAND IN ETHYLENE OLIGOMERIZATION

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Hongfei Wu, Beijing (CN); Mingfang Zheng, Beijing (CN); Songshuang Hu, Beijing (CN); Tonglin Li, Beijing (CN); Jun Liu, Beijing (CN); Ke Xu, Beijing (CN); Xiaoqing Wang, Beijing (CN); Feng Pan, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 75 days.

(21) Appl. No.: 17/310,093

(22) PCT Filed: Oct. 30, 2019

(86) PCT No.: PCT/CN2019/114393
§ 371 (c)(1),
(2) Date: Jul. 15, 2021

(87) PCT Pub. No.: WO2020/147372
PCT Pub. Date: Jul. 23, 2020

(65) Prior Publication Data
US 2022/0072523 A1 Mar. 10, 2022

(30) Foreign Application Priority Data

Jan. 15, 2019 (CN) .......................... 201910036068.8
Jan. 15, 2019 (CN) .......................... 201910037044.4

(51) Int. Cl.
*B01J 31/24* (2006.01)
*C07C 2/36* (2006.01)

(52) U.S. Cl.
CPC ............. *B01J 31/2409* (2013.01); *C07C 2/36* (2013.01); *C07C 2531/24* (2013.01)

(58) Field of Classification Search
None
See application file for complete search history.

(56) References Cited

U.S. PATENT DOCUMENTS

| 3,676,523 | A | 7/1972 | Mason |
| 3,686,351 | A | 8/1972 | Mason |
| 2003/0166456 | A1 | 9/2003 | Wass |
| 2008/0242811 | A1 | 10/2008 | Gao et al. |
| 2010/0137669 | A1 | 6/2010 | Han et al. |
| 2015/0045603 | A1 | 2/2015 | Han et al. |

FOREIGN PATENT DOCUMENTS

| CN | 1401666 | A | 3/2003 |
| CN | 1769270 | A | 5/2006 |
| CN | 101646684 | A | 2/2010 |
| CN | 104169003 | A | 11/2014 |
| CN | 105562097 | A | 5/2016 |
| CN | 107282133 | A | 10/2017 |
| IN | 101720253 | A | 6/2010 |
| JP | 1160627 | A | 3/1999 |
| WO | 1999001550 | A | 1/1999 |
| WO | 1999023096 | A | 5/1999 |
| WO | 2004056478 | A | 7/2004 |
| WO | 2008119153 | A1 | 10/2008 |
| WO | 2009006979 | A2 | 1/2009 |

OTHER PUBLICATIONS

Sung-Kwan Kim et. al., "Bimetallic Ethylene Tetramerization Catalysts Derived from Chiral DPPDME Ligands: Syntheses, Structural Characterizations, and Catalytic Performance of [(DPPDME)CrCl3]2 (DPPDME = S,S- and R,R-chiraphos and meso-achiraphos)", Organometallics, vol. 29, No. 22, Oct. 13, 2010, pp. 5805-5811.

*Primary Examiner* — Yun Qian
(74) *Attorney, Agent, or Firm* — NKL Law; Allen Xue

(57) ABSTRACT

A halogen-containing compound represented by a formula I and a use thereof as a ligand of an ethylene oligomerization catalyst composition, an ethylene oligomerization catalyst composition comprising the halogen-containing compound, and an ethylene oligomerization method, ethylene trimerization method and ethylene tetramerization method using the catalyst composition are provided. Serving as the ligand of the ethylene oligomerization catalyst, the halogen-containing polymer may effectively improve the catalytic performance of a catalyst system, especially by displaying a significantly improved catalytic performance in an ethylene oligomerization reaction. The maximum catalyst activity may exceed $4\times10^8$ g·mol(Cr)$^{-1}$·h$^{-1}$, and the total selectivity of 1-hexene and 1-octene exceeds 92 wt %. In a C6 product, the content of 1-hexene may reach about 97%, and in a C8 product, the content of 1-octene may reach more than 98%.

15 Claims, No Drawings

HALOGEN-CONTAINING COMPOUND AND USE THEREOF AS CATALYST LIGAND IN ETHYLENE OLIGOMERIZATION

FIELD OF THE INVENTION

The present invention relates to a halogen-containing compound, and also relates to use of the halogen-containing compound as a ligand of an ethylene oligomerization catalyst composition. The present invention further relates to an ethylene oligomerization catalyst composition, and an ethylene oligomerization method, ethylene trimerization method and ethylene tetramerization method using the catalyst composition.

BACKGROUND OF THE INVENTION

Ethylene oligomerization is one of the most important reactions in an olefin polymerization industry. An inexpensive small-molecule olefin may be converted into high value-added products, such as 1-octene and 1-hexene, by the oligomerization. The 1-octene and 1-hexene, as important organic raw materials and chemical intermediates, are mainly used in the field of production of high-quality polyethylene (PE). A linear low-density polyethylene (LL-DPE) produced by copolymerization of 1-hexene or 1-octene and ethylene may significantly improve various properties of PE, especially the mechanical properties, optical properties, and tear resistance and impact resistance of polyethylene. The resulting product is greatly suitable for a packaging film and agricultural covering-film such as greenhouses and sheds.

Recently, with the continuous development of the polyolefin industry, there is a rapidly increasing demand for α-olefin in the worldwide. Most of the α-olefins are prepared by ethylene oligomerization.

Since the 1970s, the research on polymerization and oligomerization of olefins catalyzed by a transition metal complex has gradually attracted the attention of scientists. Researchers have begun to study novel catalysts and improve existing catalysts to increase the activity of catalysts and the selectivity of catalytic products.

Among the explorations, a nickel-based cationic catalytic system is an earliest, fastest-developing, and relatively concentrated catalytic system, as described in U.S. Pat. Nos. 3,686,351 and 3,676,523, and a Shell's SHOP process based on the patent technology. In the Shell's SHOP process, an O—P bridged ligand is involved, however the catalyst contains a toxic organophosphorus group and has complicated synthesis steps and a poor stability.

Subsequently, researchers further developed an O—O, P—N, P—P and N—N type nickel coordination catalyst, as described in JP11060627, WO9923096, WO991550, CN1401666 and CN1769270. However, the catalysts obtained from the above patents generally have a disadvantage of being prepared in a relatively complex way.

A catalyst with a PNP backbone is disclosed in Patent WO04056478 owned by Sasol Company. In the ethylene tetramerization reaction, the selectivity of a C8 component is about 66 wt %, and the selectivity of a C6 component is about 21 wt %, wherein the content of 1-hexene in the C6 component is only 82%, and the total selectivity of 1-hexene and 1-octene is about 84%.

A catalyst with a PCCP symmetric backbone is disclosed in US20100137669. In the ethylene tetramerization reaction, the catalyst is more stable than the PNP system, but the total selectivity of 1-hexene and 1-octene does not exceed 85%.

In the above-described reaction systems, although by-products such as cycloolefin and a cyclized product existing in the C6 product may be removed by means of separation and purification or the like, it is unfavorable to the economics of the entire process.

SUMMARY OF THE INVENTION

In view of the above-mentioned deficiency of the prior art, the present inventor conducted in-depth research on phosphorus-containing catalysts for ethylene oligomerization, and found introduction of a ligand with an asymmetric bisphosphine skeleton and a halogen substituent into a catalyst system may effectively improve the catalytic performance of the catalyst system, especially the catalytic performance in the ethylene trimerization and tetramerization reaction, display significantly improved activity and selectivity, and significantly reduce production of by-products such as cycloolefin and a cyclized product.

According to a first aspect, the present invention provides a halogen-containing compound represented by a formula I,

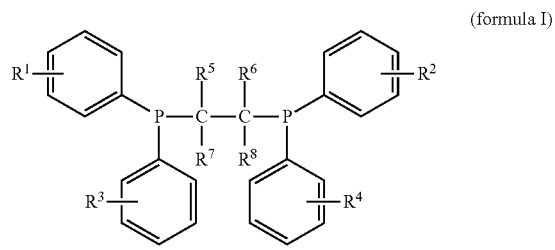

(formula I)

in the formula I, $R^1$, $R^2$, $R^3$ and $R^4$ are the same or different, each independently being halogen; $R^5$, $R^6$, $R^7$ and $R^8$ are each independently hydrogen, $C_1$-$C_{12}$ alkyl, $C_3$-$C_{12}$ cycloalkyl or $C_6$-$C_{20}$ aryl, and $R^5$ and $R^6$ are different or $R^7$ and $R^8$ are different.

According to a second aspect, the present invention provides use of the halogen-containing compound according to the first aspect of the present invention as a ligand of an ethylene oligomerization catalyst composition.

According to a third aspect, the present invention provides an ethylene oligomerization catalyst composition, including the halogen-containing compound according to the first aspect of the present invention, a transition metal compound and a co-catalyst.

According to a fourth aspect, the present invention provides an ethylene oligomerization method, which includes a step of contacting ethylene with the catalyst composition according to the third aspect of the present invention.

According to a fifth aspect, the present invention provides an ethylene trimerization method, which includes a step of contacting ethylene with the catalyst composition according to the third aspect of the present invention at a temperature of 60° C. or above.

According to a sixth aspect, the present invention provides an ethylene tetramerization method, which includes a step of contacting ethylene with the catalyst composition according to the third aspect of the present invention at a temperature of lower than 60° C.

The halogen-containing compound according to the present invention, serving as a ligand of the catalyst for ethylene oligomerization, may effectively improve the catalytic performance of a catalyst system, especially by displaying a significantly improved catalytic performance in an ethylene oligomerization reaction. The catalyst activity is higher than $0.8 \times 10^8$ g·mol(Cr)$^{-1}$·h$^{-1}$, and the maximum catalyst activity may exceed $4 \times 10^8$ g·mol(Cr)$^{-1}$·h$^{-1}$, and the total selectivity of 1-hexene and 1-octene exceeds 92 wt %, and in a C6 product, the content of 1-hexene may reach about 97%, and in a C8 product, the content of 1-octene may reach 98% or above.

In addition, when the catalyst composition of the present invention is used for the oligomerization of ethylene, a high initiation speed is achieved, and the absorption of ethylene can reach the maximum in a short time (within 5 minutes), and maintain for a long time (0.5 hours or above). It is showed that the catalyst composition according to the present invention initiates quickly and has high stability during the polymerization reaction.

Therefore, the catalyst composition according to the present invention has the characteristics of high catalytic activity and high selectivity, and has good industrial application prospects and economic value.

DETAILED DESCRIPTION OF THE EMBODIMENTS

The endpoints and any values of the ranges disclosed herein are not limited to the precise ranges or values, and these ranges or values should be understood to include values close to these ranges or values. For numerical ranges, endpoints values of each range, endpoint values and an individual point value of each range, and individual point values may be combined with each other to obtain one or more new numerical ranges, which should be considered as being specifically disclosed herein.

In the present invention, the term "$C_1$-$C_{12}$ alkyl" includes $C_1$-$C_{12}$ linear alkyl and $C_3$-$C_{12}$ branched alkyl. Specific examples thereof may include, but are not limited to, methyl, ethyl, n-propyl, isopropyl, n-butyl, sec-butyl, isobutyl, tert-butyl, n-pentyl, 2-methylbutyl, 3-methylbutyl, 2,2-dimethylpropyl, n-hexyl, 2-methylpentyl, 3-methylpentyl, 4-methylpentyl, 2,3-dimethylbutyl, 2,2-dimethylbutyl, 3,3-dimethylbutyl, 2-ethylbutyl, n-heptyl, 2-methylhexyl, 3-methylhexyl, 4-methylhexyl, 5-methylhexyl, 2,2-dimethylpentyl, 2,3-dimethylpentyl, 2,4-dimethylpentyl, 3,3-dimethylpentyl, 3,4-dimethylpentyl, 4,4-dimethylpentyl, 2-ethylpentyl, 3-ethylpentyl, n-octyl, 2-methylheptyl, 3-methylheptyl, 4-methylheptyl, 5-methylheptyl, 6-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 5,5-dimethylhexyl, 2-ethylhexyl, 3-ethylhexyl, 4-ethylhexyl, 2-n-propylpentyl, 2-isopropylpentyl, octyl (including various isomers of octyl), decyl (including various isomers of decyl), undecyl (including various isomers of undecyl) and dodecyl (including various isomers of dodecyl).

In the present invention, the term "$C_3$-$C_{12}$ cycloalkyl" includes substituted or unsubstituted cycloalkyl. The substituted cycloalkyl refers to a group in which at least one hydrogen atom bonded to a carbon atom on the ring is replaced by a substituent that may be $C_1$-$C_6$ alkyl, and specific examples of the substituent may include, but are not limited to: methyl, ethyl, n-propyl, isopropyl, n-butyl, sec-butyl, isobutyl, tert-butyl, n-pentyl, isopentyl, tert-pentyl, neopentyl and hexyl (including various isomers of hexyl). Specific examples of the $C_3$-$C_{12}$ cycloalkyl may include, but are not limited to: cyclopropyl, cyclobutyl, cyclopentyl, cyclohexyl, methylcyclohexyl, ethylcyclohexyl, propylcyclohexyl, and butylcyclohexyl.

In the present invention, the term "$C_6$-$C_{20}$ aryl" includes substituted or unsubstituted aryl. The substituted aryl refers to a group in which at least one hydrogen atom on the aromatic ring is replaced by a substituent that may be $C_1$-$C_6$ alkyl and/or a halogen group, and specific examples of the substituent may include, but are not limited to: methyl, ethyl, n-propyl, isopropyl, n-butyl, sec-butyl, isobutyl, tert-butyl, n-pentyl, isopentyl, tert-pentyl, neopentyl, hexyl (including various isomers of hexyl), chlorine, bromine and iodine. Specific examples of the $C_6$-$C_{20}$ aryl may include, but are not limited to: phenyl, naphthyl, tolyl, ethylphenyl, chlorophenyl, or naphthyl.

According to a first aspect, the present invention provides a halogen-containing compound represented by a formula I,

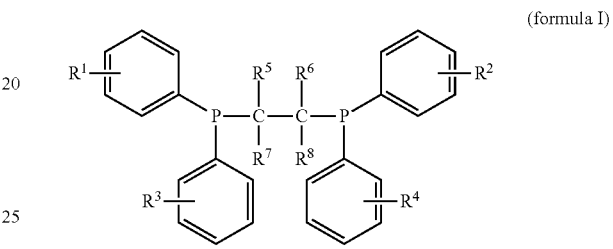

(formula I)

in the formula I, $R^1$, $R^2$, $R^3$ and $R^4$ may be the same or different, each independently being halogen; $R^5$, $R^6$, $R^7$ and $R^8$ are each independently hydrogen, $C_1$-$C_{12}$ alkyl, $C_3$-$C_{12}$ cycloalkyl or $C_6$-$C_{20}$ aryl, and $R^5$ and $R^6$ are different or $R^7$ and $R^8$ are different.

In the formula I, P represents phosphorus.

In the formula I, $R^1$, $R^2$, $R^3$ and $R^4$ may be the same or different, each independently being halogen, such as fluorine, chlorine, bromine or iodine. Preferably, $R^1$, $R^2$, $R^3$ and $R^4$ may be the same or different, each independently being chlorine or fluorine. More preferably, all of $R^1$, $R^2$, $R^3$ and $R^4$ are fluorine.

In the formula I, at least one of $R^1$, $R^2$, $R^3$, and $R^4$ is an ortho-substituent. Preferably, all of $R^1$, $R^2$, $R^3$ and $R^4$ are an ortho-substituent.

Preferably, in the formula I, $R^5$, $R^6$, $R^7$ and $R^8$ are each independently hydrogen, $C_1$-$C_8$ alkyl, $C_3$-$C_8$ cycloalkyl or $C_6$-$C_{16}$ aryl, and $R^5$ and $R^6$ are different or $R^7$ and $R^8$ are different.

More preferably, in the formula I, $R^5$, $R^6$, $R^7$ and $R^8$ are each independently hydrogen, $C_1$-$C_6$ alkyl, $C_3$-$C_6$ cycloalkyl or $C_6$-$C_{12}$ aryl, and $R^5$ and $R^6$ are different or $R^7$ and $R^8$ are different.

Further preferably, in the formula I, $R^5$, $R^6$, $R^7$ and $R^8$ are each independently hydrogen, methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl, and $R^5$ and $R^6$ are different or $R^7$ and $R^8$ are different.

Still more preferably, in the formula I, $R^5$, $R^6$, $R^7$ and $R^8$ are each independently hydrogen, tert-butyl, cyclohexyl, phenyl, isopropyl or ethyl, and $R^5$ and $R^6$ are different or $R^7$ and $R^8$ are different.

Particularly preferably, in the formula I, $R^5$, $R^6$, $R^7$ and $R^8$ are each independently hydrogen, tert-butyl, cyclohexyl or phenyl, and $R^5$ and $R^6$ are different or $R^7$ and $R^8$ are different.

In the formula I, one, two or three of $R^5$, $R^6$, $R^7$ and $R^8$ are preferably hydrogen.

In a preferred example, in the formula I, $R^5$ is $C_1$-$C_{12}$ alkyl, $C_3$-$C_{12}$ cycloalkyl or $C_6$-$C_{20}$ aryl, and $R^6$, $R^7$ and $R^8$ are hydrogen. Preferably, in the formula I, $R^5$ is $C_1$-$C_8$ alkyl, $C_3$-$C_8$ cycloalkyl or $C_6$-$C_{16}$ aryl, and $R^6$, $R^7$ and $R^8$ are hydrogen. More preferably, in the formula I, $R^5$ is $C_1$-$C_6$ alkyl, $C_3$-$C_6$ cycloalkyl or $C_6$-$C_{12}$ aryl, and $R^6$, $R^7$ and $R^8$ are hydrogen. Further preferably, in the formula I, $R^5$ is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl, and $R^6$, $R^7$ and $R^8$ are hydrogen. Still more preferably, in the formula I, $R^5$ is tert-butyl, cyclohexyl, phenyl, isopropyl or ethyl, and $R^6$, $R^7$ and $R^8$ are hydrogen. Particularly preferably, in the formula I, $R^5$ is tert-butyl, cyclohexyl or phenyl, and $R^6$, $R^7$ and $R^8$ are hydrogen.

According to the first aspect of the present invention, in a preferred embodiment, the halogen-containing compound is a compound represented by a formula II,

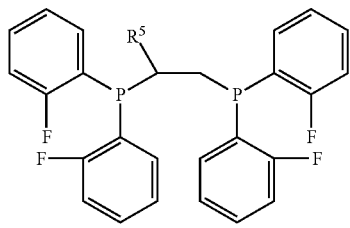

(formula II)

in the formula II, $R^5$ is $C_1$-$C_{12}$ alkyl, $C_3$-$C_{12}$ cycloalkyl or $C_6$-$C_{20}$ aryl.

Preferably, in the formula II, $R^5$ is $C_1$-$C_8$ alkyl, $C_3$-$C_8$ cycloalkyl or $C_6$-$C_{16}$ aryl. More preferably, in the formula II, $R^5$ is $C_1$-$C_6$ alkyl, $C_3$-$C_6$ cycloalkyl or $C_6$-$C_{12}$ aryl. Further preferably, in the formula II, $R^5$ is methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl or naphthyl. Still more preferably, in the formula II, $R^5$ is tert-butyl, cyclohexyl, phenyl, isopropyl or ethyl. Particularly preferably, in the formula II, $R^5$ is tert-butyl, cyclohexyl or phenyl.

The halogen-containing compound according to the present invention may be prepared with reference to the method disclosed in ACS Catalysis, 2013, 3, 2311-2317. Specifically, the halogen-containing compound may be prepared by a method including the following steps: methylsulfonyl chloride is subjected to a first contact with alkyl ethylene glycol represented by a formula III to obtain a compound represented by a formula IV; the compound represented by the formula IV is subjected to a second contact with LiP(2-F-Ph)$_2$; and the mixture obtained by the second contact is separated to yield the halogen-containing compound represented by the formula I.

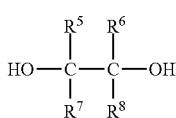

(formula III)

(formula IV)

In the formulae III and IV, $R^5$, $R^6$, $R^7$ and $R^8$ are defined as same as those of $R^5$, $R^6$, $R^7$ and $R^8$ in the formula I, and will not be described in detail herein. In the formula IV, Ms is an abbreviation for methylsulfonyl, which refers to $CH_3SO_2$—.

The first contact is performed in a halogenated alkane as a solvent, and the halogenated alkane may be, for example, dichloromethane. Methylsulfonyl chloride is mixed with the solvent, then the mixture is mixed with alkyl ethylene glycol represented by the formula III, and a reaction is carried out. The alkyl ethylene glycol is preferably added dropwise to a solution containing methylsulfonyl chloride. The first contact may be performed at a temperature of −10° C. to 30° C. Preferably, the first contact is carried out sequentially at a temperature of −5° C. to 5° C. and 15° C. to 30° C., wherein the reaction may be carried out at −5° C. to 5° C. for 0.5-2 hours, and at 15° C. to 30° C. for 1-3 hours.

After the first contact is completed, an acid may be added to the reaction mixture obtained by the first contact. Then, the reaction mixture is divided into an aqueous phase and an organic phase, and the aqueous phase is extracted with a halogenated alkane (preferably dichloromethane), and organic phases are mixed. The mixed organic phase is neutralized, and then washed, and dried, and the solvent is removed, and the residue obtained is the compound represented by the formula IV. The molar ratio of LiP(2-F-Ph)$_2$ to the compound represented by the formula IV may be 2-3:1. The second contact may be performed at a temperature of 15-30° C. The second contact may be carried out in an oxygen-containing heterocyclic compound, preferably in tetrahydrofuran.

The halogen-containing compound represented by the formula I may be separated from the reaction mixture obtained by the second contact through conventional methods. For example, the solvent is removed from the reaction mixture obtained by the second contact, and then precipitation is performed with water. The precipitate is collected, and subjected to column separation to obtain the halogen-containing compound represented by the formula I.

The reaction mechanism for preparing the halogen-containing compound represented by the formula II is exemplarily shown as follows:

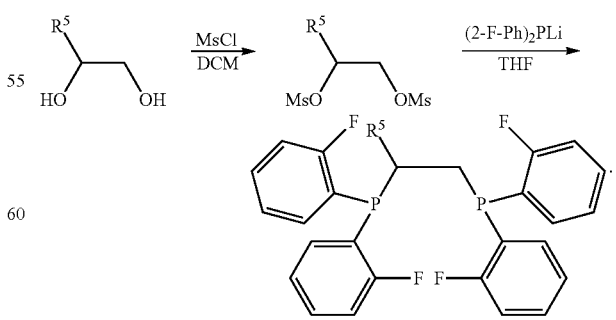

The halogen-containing compound according to the present invention is particularly suitable as a ligand of a catalyst for ethylene oligomerization. When the ligand of the catalyst contains the halogen-containing compound, the catalytic performance of the catalyst is significantly improved.

According to a second aspect, the present invention provides use of the halogen-containing compound according to the first aspect of the present invention as a ligand of an ethylene oligomerization catalyst composition.

The halogen-containing compound according to the present invention may be used in combination with a transition metal compound and a co-catalyst commonly used in ethylene oligomerization.

In a preferred embodiment, the catalyst composition contains a transition metal compound, a co-catalyst and the halogen-containing compound.

A transition metal element in the transition metal compound may be chromium, molybdenum, iron, titanium, zirconium or nickel. Accordingly, the transition metal compound may be at least one selected from the group consisting of a chromium compound, a molybdenum compound, an iron compound, a titanium compound, a zirconium compound, and a nickel compound. The transition metal compound may be at least one selected from the group consisting of transition metal acetylacetonate, transition metal carboxylate, and a complex of a transition metal and tetrahydrofuran. The transition metal compound is preferably at least one selected from the group consisting of chromium acetylacetonate, chromium isooctanoate, tris(tetrahydrofuran) chromium trichloride, and bis(tetrahydrofuran) chromium dichloride. The transition metal compound is more preferably chromium acetylacetonate.

A molar ratio of the halogen-containing compound to the transition metal compound may be 1:0.1-10, for example: 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

Preferably, the molar ratio of the halogen-containing compound to the transition metal compound is 1:0.25-2. More preferably, the molar ratio of the halogen-containing compound to the transition metal compound is 1:0.5-2. Further preferably, the molar ratio of the halogen-containing compound to the transition metal compound is 1:0.5-1. Still more preferably, the molar ratio of the halogen-containing compound to the transition metal compound is 1:0.5-0.8.

The co-catalyst may be an aluminum-containing co-catalyst. Preferably, the co-catalyst is an organoaluminum compound. More preferably, the co-catalyst is at least one selected from the group consisting of alkyl aluminum, alkoxy aluminum and alkyl aluminum halide. Further preferably, the co-catalyst is at least one selected from the group consisting of methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane and modified methylaluminoxane. Still more preferably, the co-catalyst is at least one selected from the group consisting of modified methylaluminoxane, methylaluminoxane and triethylaluminum. Particularly preferably, the co-catalyst is modified methylaluminoxane. In the present invention, "modified methylaluminoxane" refers to methylaluminoxane which is modified with an alkyl group, for example, methylaluminoxane modified with butyl. The modified methylaluminoxane may be modified methylaluminoxane purchased from Akzo Nobel.

A molar ratio of the halogen-containing compound to the co-catalyst may be 1:1-1000. Preferably, the molar ratio of the halogen-containing compound to the co-catalyst is 1:10-700. More preferably, the molar ratio of the halogen-containing compound to the co-catalyst is 1:100-500, for example: 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:205, 1:210, 1:215, 1:220, 1:225, 1:230, 1:235, 1:240, 1:245, 1:250, 1:255, 1:260, 1:265, 1:270, 1:275, 1:280, 1:285, 1:290, 1:295, 1:300, 1:305, 1:310, 1:315, 1:320, 1:325, 1:330, 1:335, 1:340, 1:345, 1:350, 1:355, 1:360, 1:365, 1:370, 1:375, 1:380, 1:385, 1:390, 1:395, 1:400, 1:405, 1:410, 1:415, 1:420, 1:425, 1:430, 1:435, 1:440, 1:445, 1:450, 1:455, 1:460, 1:465, 1:470, 1:475, 1:480, 1:485, 1:490, 1:495 or 1:500.

Further preferably, the molar ratio of the halogen-containing compound to the co-catalyst is 1:150-300. Still more preferably, the molar ratio of the halogen-containing compound to the co-catalyst is 1:200-280.

According to a third aspect, the present invention provides an ethylene oligomerization catalyst composition. The composition contains the halogen-containing compound represented by the formula I, a transition metal compound and a co-catalyst. The halogen-containing compound and the preparation method thereof have been described above, and will not be described in detail here.

The transition metal element in the transition metal compound may be chromium, molybdenum, iron, titanium, zirconium or nickel. Accordingly, the transition metal compound may be at least one selected from the group consisting of a chromium compound, a molybdenum compound, an iron compound, a titanium compound, a zirconium compound, and a nickel compound.

The transition metal compound may be at least one selected from the group consisting of transition metal acetylacetonate, transition metal carboxylate, and a complex of a transition metal and tetrahydrofuran.

The transition metal compound is preferably at least one selected from the group consisting of chromium acetylacetonate, chromium isooctanoate, tris(tetrahydrofuran) chromium trichloride, and bis(tetrahydrofuran) chromium dichloride. The transition metal compound is more preferably chromium acetylacetonate.

The molar ratio of the halogen-containing compound to the transition metal compound may be 1:0.1-10, for example: 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

Preferably, the molar ratio of the halogen-containing compound to the transition metal compound is 1:0.25-2. More preferably, the molar ratio of the halogen-containing compound to the transition metal compound is 1:0.5-2. Further preferably, the molar ratio of the halogen-containing compound to the transition metal compound is 1:0.5-1. Still more preferably, the molar ratio of the halogen-containing compound to the transition metal compound is 1:0.5-0.8.

The co-catalyst may be an aluminum-containing co-catalyst. Preferably, the co-catalyst is an organoaluminum compound. More preferably, the co-catalyst is at least one selected from the group consisting of alkyl aluminum, alkoxy aluminum and alkyl aluminum halide. Further preferably, the co-catalyst is at least one selected from the group consisting of methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane and modified methylaluminoxane. Still more preferably, the co-catalyst is at least one selected from the group consisting of modified methylaluminoxane, methylaluminoxane and triethylaluminum. Particularly preferably, the co-catalyst is modified methylaluminoxane.

The molar ratio of the halogen-containing compound to the co-catalyst may be 1:1-1000. Preferably, the molar ratio of the halogen-containing compound to the co-catalyst is 1:10-700. More preferably, the molar ratio of the halogen-containing compound to the co-catalyst is 1:100-500, for example: 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:205, 1:210, 1:215, 1:220, 1:225, 1:230, 1:235, 1:240, 1:245, 1:250, 1:255, 1:260, 1:265, 1:270, 1:275, 1:280, 1:285, 1:290, 1:295, 1:300, 1:305, 1:310, 1:315, 1:320, 1:325, 1:330, 1:335, 1:340, 1:345, 1:350, 1:355, 1:360, 1:365, 1:370, 1:375, 1:380, 1:385, 1:390, 1:395, 1:400, 1:405, 1:410, 1:415, 1:420, 1:425, 1:430, 1:435, 1:440, 1:445, 1:450, 1:455, 1:460, 1:465, 1:470, 1:475, 1:480, 1:485, 1:490, 1:495 or 1:500.

Further preferably, the molar ratio of the halogen-containing compound to the co-catalyst is 1:150-300. Still more preferably, the molar ratio of the halogen-containing compound to the co-catalyst is 1:200-280.

According to a fourth aspect, the present invention provides an ethylene oligomerization method. The method includes a step of contacting ethylene with the catalyst composition according to the third aspect of the present invention.

According to the ethylene oligomerization method of the present invention, the contacting is preferably carried out in at least one organic solvent. The organic solvent is a solvent capable of dissolving an oligomerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-methylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trimethylpentane, 2,3,3-trimethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trimethylcyclohexane, such as 1,2,3-trimethylcyclohexane, 1,2,4-trimethylcyclohexane, 1,2,5-trimethylcyclohexane, 1,3,5-trimethylcyclohexane), decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-diethylcyclohexane, 1,3-diethylcyclohexane, 1,4-diethylcyclohexane, n-butylcyclohexane, isobutylcyclohexane, tert-butylcyclohexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 μmol/L. Specifically, the organic solvent is used in an amount such that the concentration of the catalyst composition, in terms of the transition metal element in the transition metal compound, is 1 μmol/L, 2 μmol/L, 3 μmol/L, 4 μmol/L, 5 μmol/L, 6 μmol/L, 7 μmol/L, 8 μmol/L, 9 μmol/L. L, 10 μmol/L, 11 μmol/L, 12 μmol/L, 13 μmol/L, 14 mol/L, 15 μmol/L, 16 μmol/L, 17 μmol/L, 18 μmol/L, 19 μmol/L or 20 μmol/L. Preferably, the amount of the organic solvent is such that the concentration of the catalyst composition, in terms of the transition metal element in the transition metal compound, is 5-10 μmol/L.

According to the ethylene oligomerization method of the present invention, the contacting may be carried out at a temperature of 0-200° C., for example: 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., 144° C., 145°

C., 146° C., 147° C., 148° C., 149° C., 150° C., 151° C., 152° C., 153° C., 154° C., 155° C., 156° C., 157° C., 158° C., 159° C., 160° C., 161° C., 162° C., 163° C., 164° C., 165° C., 166° C., 167° C., 168° C., 169° C., 170° C., 171° C., 172° C., 173° C., 174° C., 175° C., 176° C., 177° C., 178° C., 179° C., 180° C., 181° C., 182° C., 183° C., 184° C., 185° C., 186° C., 187° C., 188° C., 189° C., 190° C., 191° C., 192° C., 193° C., 194° C., 195° C., 196° C., 197° C., 198° C., 199° C. or 200° C.

Preferably, the contacting is carried out at a temperature of 0-100° C. More preferably, the contacting is carried out at a temperature of 30-90° C.

According to the ethylene oligomerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-10 MPa. More preferably, the pressure of the ethylene is 2-8 MPa.

According to the ethylene oligomerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

According to a fifth aspect, the present invention provides an ethylene trimerization method. The method includes a step of contacting ethylene with the catalyst composition according to the third aspect of the present invention at a temperature of 60° C. or above. In the present invention, "ethylene trimerization" means that the product formed by the ethylene trimerization is mainly C6 olefin (i.e., hexene), and the content of the C6 olefin may be 50% by weight or more, preferably 60% by weight or more.

According to the ethylene trimerization method of the present invention, the temperature for the contacting is preferably 60-90° C., and may be, for example, 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or 90° C. More preferably, the temperature for the contacting is 70-90° C.

According to the ethylene trimerization method of the present invention, the contacting is preferably carried out in at least one organic solvent. The organic solvent is a solvent capable of dissolving an oligomerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-methylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trimethylpentane, 2,3,3-trimethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trimethylcyclohexane, such as 1,2,3-trimethylcyclohexane, 1,2,4-trimethylcyclohexane, 1,2,5-trimethylcyclohexane, 1,3,5-trimethylcyclohexane), decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-diethylcyclohexane, 1,3-diethylcyclohexane, 1,4-diethylcyclohexane, n-butylcyclohexane, isobutylcyclohexane, tert-butylcyclohexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 μmol/L. Specifically, the organic solvent is used in an amount such that the concentration of the catalyst composition, in terms of the transition metal element in the transition metal compound, is 1 μmol/L, 2 μmol/L, 3 μmol/L, 4 μmol/L, 5 μmol/L, 6 μmol/L, 7 μmol/L, 8 μmol/L, 9 μmol/L, 10 μmol/L, 11 μmol/L, 12 μmol/L, 13 μmol/L, 14 μmol/L, 15 μmol/L, 16 μmol/L, 17 μmol/L, 18 μmol/L, 19 μmol/L or 20 μmol/L. Preferably, the organic solvent is used in an amount such that the concentration of the catalyst composition, in terms of the transition metal element in the transition metal compound, is 5-10 μmol/L.

According to the ethylene trimerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-5 MPa. More preferably, the pressure of the ethylene is 1-4 MPa. Further preferably, the pressure of the ethylene is 2-3 MPa.

According to the ethylene trimerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

According to a sixth aspect, the present invention provides an ethylene tetramerization method. The method includes a step of contacting ethylene with the catalyst composition according to the third aspect of the present invention at a temperature of lower than 60° C. In the present invention, "ethylene tetramerization" means that the product formed by the ethylene tetramerization is mainly C8 olefin (i.e., octene), and the content of the C8 olefin may be 50% by weight or more, preferably 55% by weight or more.

According to the ethylene tetramerization method of the present invention, the temperature for the contacting is preferably 30-50° C., and may be, for example, 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

According to the ethylene tetramerization method of the present invention, the contacting is preferably carried out in at least one organic solvent. The organic solvent is a solvent capable of dissolving a tetramerization product, and may be at least one selected from the group consisting of an alkane, a cycloalkane and an aromatic hydrocarbon, preferably at least one selected from the group consisting of $C_6$-$C_{12}$ alkane, $C_6$-$C_{12}$ cycloalkane, and $C_6$-$C_{12}$ aromatic hydrocarbon. Specific examples of the organic solvent may include, but are not limited to: hexane, 2-methylpentane, 3-methylpentane, 2,3-dimethylbutane, cyclohexane, methylcyclopentane, heptane, 2-methylhexane, 3-methylhexane, methylcyclohexane, 2-ethylpentane, 3-ethylpentane, 2,3-dimethylpentane, 2,4-dimethylpentane, octane, 2-methylheptane, 3-methylheptane, 4-methylheptane, 2,3-dimethylhexane, 2,4-dimethylhexane, 2,5-dimethylhexane, 3-ethylhexane, 2,2,3-trimethylpentane, 2,3,3-trimethylpentane, 2,4,4-trimethylpentane, 2-methyl-3-ethylpentane, nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, isopropylcyclohexane, trimethylcyclohexane (including various isomers of trimethylcyclohexane, such as 1,2,3-trimethylcyclohexane, 1,2,4-trimethylcyclohexane, 1,2,5-trimethylcyclohexane, 1,3,5-trimethylcyclohexane), decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, 1,2-diethylcyclohexane, 1,3-diethylcyclohexane, 1,4-diethylcyclohexane, n-butylcyclohexane, isobutylcyclohexane, tert-butylcyclohexane, tetramethylcyclohexane (including various isomers of tetramethylcyclohexane, such as 1,2,3,4-tetramethylcyclohexane, 1,2,4,5-tetramethylcyclohexane, 1,2,3,5-tetramethylcyclohexane), toluene, ethylbenzene and xylene (including o-xylene, m-xylene and p-xylene). The organic solvent is more preferably at least one selected from the group consisting of methylcyclohexane, heptane, cyclohexane, toluene, and xylene.

In the present invention, the amount of the organic solvent is not particularly limited, and may be conventionally selected. Generally, the organic solvent is used in an amount such that the concentration of the catalyst composition, in terms of the transition metal element in the transition metal compound, is 1-20 μmol/L. Specifically, the organic solvent is used in an amount such that the concentration of the catalyst composition, in terms of the transition metal element in the transition metal compound, is 1 μmol/L, 2 μmol/L, 3 μmol/L, 4 μmol/L, 5 μmol/L, 6 μmol/L, 7 μmol/L, 8 μmol/L, 9 μmol/L, 10 μmol/L, 11 μmol/L, 12 μmol/L, 13 μmol/L, 14 μmol/L, 15 μmol/L, 16 μmol/L, 17 μmol/L, 18 μmol/L, 19 μmol/L or 20 μmol/L. Preferably, the organic solvent is used in an amount such that the concentration of the catalyst composition, in terms of the transition metal element in the transition metal compound, is 5-10 μmol/L.

According to the ethylene tetramerization method of the present invention, the pressure of the ethylene may be 0.1-20 MPa, for example: 0.1 MPa, 0.2 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 2.1 MPa, 2.2 MPa, 2.3 MPa, 2.4 MPa, 2.5 MPa, 2.6 MPa, 2.7 MPa, 2.8 MPa, 2.9 MPa, 3 MPa, 3.1 MPa, 3.2 MPa, 3.3 MPa, 3.4 MPa, 3.5 MPa, 3.6 MPa, 3.7 MPa, 3.8 MPa, 3.9 MPa, 4 MPa, 4.1 MPa, 4.2 MPa, 4.3 MPa, 4.4 MPa, 4.5 MPa, 4.6 MPa, 4.7 MPa, 4.8 MPa, 4.9 MPa, 5 MPa, 5.1 MPa, 5.2 MPa, 5.3 MPa, 5.4 MPa, 5.5 MPa, 5.6 MPa, 5.7 MPa, 5.8 MPa, 5.9 MPa, 6 MPa, 6.1 MPa, 6.2 MPa, 6.3 MPa, 6.4 MPa, 6.5 MPa, 6.6 MPa, 6.7 MPa, 6.8 MPa, 6.9 MPa, 7 MPa, 7.1 MPa, 7.2 MPa, 7.3 MPa, 7.4 MPa, 7.5 MPa, 7.6 MPa, 7.7 MPa, 7.8 MPa, 7.9 MPa, 8 MPa, 8.1 MPa, 8.2 MPa, 8.3 MPa, 8.4 MPa, 8.5 MPa, 8.6 MPa, 8.7 MPa, 8.8 MPa, 8.9 MPa, 9 MPa, 9.1 MPa, 9.2 MPa, 9.3 MPa, 9.4 MPa, 9.5 MPa, 9.6 MPa, 9.7 MPa, 9.8 MPa, 9.9 MPa, 10 MPa, 10.1 MPa, 10.2 MPa, 10.3 MPa, 10.4 MPa, 10.5 MPa, 10.6 MPa, 10.7 MPa, 10.8 MPa, 10.9 MPa, 11 MPa, 11.1 MPa, 11.2 MPa, 11.3 MPa, 11.4 MPa, 11.5 MPa, 11.6 MPa, 11.7 MPa, 11.8 MPa, 11.9 MPa, 12 MPa, 12.1 MPa, 12.2 MPa, 12.3 MPa, 12.4 MPa, 12.5 MPa, 12.6 MPa, 12.7 MPa, 12.8 MPa, 12.9 MPa, 13 MPa, 13.1 MPa, 13.2 MPa, 13.3 MPa, 13.4 MPa, 13.5 MPa, 13.6 MPa, 13.7 MPa, 13.8 MPa, 13.9 MPa, 14 MPa, 14.1 MPa, 14.2 MPa, 14.3 MPa, 14.4 MPa, 14.5 MPa, 14.6 MPa, 14.7 MPa, 14.8 MPa, 14.9 MPa, 15 MPa, 15.1 MPa, 15.2 MPa, 15.3 MPa, 15.4 MPa, 15.5 MPa, 15.6 MPa, 15.7 MPa, 15.8 MPa, 15.9 MPa, 16 MPa, 16.1 MPa, 16.2 MPa, 16.3 MPa, 16.4 MPa, 16.5 MPa, 16.6 MPa, 16.7 MPa, 16.8 MPa, 16.9 MPa, 17 MPa, 17.1 MPa, 17.2 MPa, 17.3 MPa, 17.4 MPa, 17.5 MPa, 17.6 MPa, 17.7 MPa, 17.8 MPa, 17.9 MPa, 18 MPa, 18.1 MPa, 18.2 MPa, 18.3 MPa, 18.4 MPa, 18.5 MPa, 18.6 MPa, 18.7 MPa, 18.8 MPa, 18.9 MPa, 19 MPa, 19.1 MPa, 19.2 MPa, 19.3 MPa, 19.4 MPa, 19.5 MPa, 19.6 MPa, 19.7 MPa, 19.8 MPa, 19.9 MPa or 20 MPa.

Preferably, the pressure of the ethylene is 0.5-8 MPa. More preferably, the pressure of the ethylene is 3-6 MPa. Further preferably, the pressure of the ethylene is 4-5 MPa.

According to the ethylene tetramerization method of the present invention, it may be performed by using a conventional method. In one embodiment, the halogen-containing compound, the transition metal compound, and the co-catalyst may be mixed, and then the mixture is added to a reactor, and is in contact with ethylene in the presence of an optional organic solvent to be subjected to an oligomerization reaction. In another embodiment, the halogen-containing compound, the transition metal compound, and the co-catalyst may be added to a reactor respectively, and be in contact with ethylene in the presence of an optional organic solvent to be subjected to an oligomerization reaction.

The present invention will be illustrated in detail below in connection with the examples, not thereby limiting the scope of the invention.

In the following examples and comparative examples, nuclear magnetic resonance spectroscopy analysis was performed by using Bruker AV400 nuclear magnetic resonance spectrometer, wherein detection conditions for nuclear magnetic resonance were: deuterated chloroform was used as a solvent and a test was performed at room temperature (25° C.). The gas chromatographic analysis was performed by HP 5890 chromatograph, wherein the detection conditions for the gas chromatograph were: a chromatographic column was an SE-54 chromatographic column, high-purity nitrogen was used as a carrier gas, and a FID detector was used; the column temperature was increased by a two-step procedure, specifically: the initial temperature was 40° C., keeping for 5 minutes, then the temperature was raised to 300° C. at 30° C./min, keeping 15 minutes.

In the following examples and comparative examples, the catalyst activity was indicated as the mass of a polymerization product generated with a unit mass of catalyst during the unit polymerization time, wherein the catalyst was measured in terms of the metal element in the transition metal compound (in terms of moles), the polymerization time was measured in hours, and the polymerization product was measured in grams. Selectivity=(the mass of the target product in the polymerization reaction product/the total mass of the polymerization reaction product)×100%.

The meanings of the abbreviations involved in the following examples and comparative examples are as follows:
$^t$Bu is tert-butyl; $^i$Pr is isopropyl; Cy is cyclohexyl; Ph is phenyl; Et is ethyl; THF is tetrahydrofuran; acac is acetylacetone; and Me is methyl.

Preparation examples 1-8 are used to prepare halogen-containing compounds according to the present invention.

Preparation Example 1

Preparation example 1 is used to prepare a halogen-containing compound I$^1$.

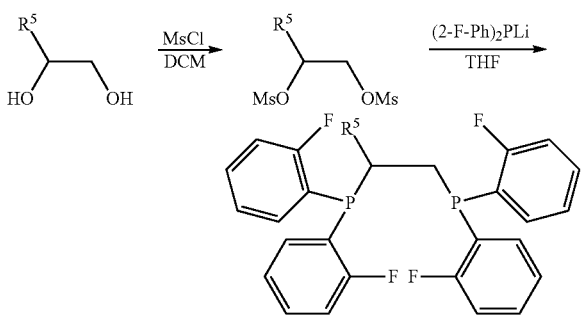

The preparation method of the halogen-containing compound I$^1$ refers to the above reaction formula, and the specific steps are as follows.

Methylsulfonyl chloride (2.15 mL, 55.2 mmol) was dissolved in 5 mL of dichloromethane, and the obtained solution was added into tert-butyl ethylene glycol (26.3 mmol) in dichloromethane dropwise at 0° C. After the reaction for 1 h, the reaction mixture was warmed up to room temperature (25° C., the same below) and continued to be stirred for 2 h. After the reaction was completed, 1M aqueous hydrochloric acid was added, and then the reaction mixture was separated into an aqueous phase and an organic phase. The aqueous phase was extracted for three times with dichloromethane and organic phases were mixed. The organic phase was washed successively with saturated aqueous $NaHCO_3$ and a saturated aqueous brine solution, and then dried over anhydrous magnesium sulfate, followed by rotary evaporation to remove the solvent. The residue was dissolved in 5 mL of tetrahydrofuran (THF), and then 5 mL of $LiP(2-F-Ph)_2$ (10 mmol) in THF was added dropwise. After the completion of the addition for 10 min, the reaction mixture was warmed up to room temperature and continued to be subjected to a reaction for 10 h. After the reaction was completed, the solvent was drained, and water was added into the residue to generate a large amount of precipitate to be filtered. The precipitate was allowed to pass through a silica gel column (petroleum ether (PE)/ethyl acetate (EA) =20:1) to obtain the halogen-containing compound $I^1$.

The prepared compound was subjected to nuclear magnetic resonance analysis, and it may be determined that the prepared compound was the compound represented by the formula II, wherein $R^5$ is $^tBu$.

$^1H$ NMR (400 MHz, $CDCl_3$): δ=7.25-6.80 (m, 16H), 3.85 (m, 1H), 2.87-2.65 (m, 2H), 1.20 (s, 9H).

Preparation Example 2

Preparation example 2 was used to prepare a halogen-containing compound $I^2$.

In this preparation example, the halogen-containing compound was prepared by the same method as in the preparation example 1, except that tert-butyl ethylene glycol was replaced with cyclohexyl ethylene glycol. The prepared compound was subjected to nuclear magnetic resonance analysis, and it may be determined that the prepared compound was the compound represented by the formula II, wherein $R^5$ is Cy.

$^1H$ NMR (400 MHz, $CDCl_3$): δ=7.30-6.83 (m, 16H), 3.16 (m, 1H), 2.95 (m, 1H), 2.68 (m, 1H), 1.80 (m, 1H), 1.25-1.55 (m, 10H).

Preparation Example 3

Preparation example 3 was used to prepare a halogen-containing compound $I^3$.

In this preparation example, the halogen-containing compound was prepared by the same method as in the preparation example 1, except that tert-buty ethylene glycol was replaced with phenyl ethylene glycol. The prepared compound was subjected to nuclear magnetic resonance analysis, and it may be determined that the prepared compound was the compound represented by the formula II, wherein $R^5$ is Ph.

$^1H$ NMR (400 MHz, $CDCl_3$): δ=7.45-7.29 (m, 4H), 7.24-6.80 (m, 16H), 6.77-6.69 (m, 1H), 3.94-3.81 (m, 1H), 2.87-2.75 (m, 1H), 2.74-2.65 (m, 1H).

Preparation Example 4

Preparation example 4 was used to prepare a halogen-containing compound $I^4$.

In this preparation example, the halogen-containing compound was prepared by the same method as in the preparation example 1, except that tert-butyl ethylene glycol was replaced with isopropyl ethylene glycol. The prepared compound was subjected to nuclear magnetic resonance analysis, and it may be determined that the prepared compound was the compound represented by the formula II, wherein $R^5$ is $^iPr$.

$^1H$ NMR (400 MHz, $CDCl_3$): δ=7.20-6.90 (m, 16H), 3.50 (m, 1H), 3.00 (m, 1H), 2.70 (m, 1H), 2.33 (m, 1H), 1.05-1.16 (m, 6H).

Preparation Example 5

Preparation example 5 was used to prepare a halogen-containing compound $I^5$.

In this preparation example, the halogen-containing compound was prepared by the same method as in the preparation example 1, except that tert-butyl ethylene glycol was replaced with ethyl ethylene glycol. The prepared compound was subjected to nuclear magnetic resonance analysis, and it may be determined that the prepared compound was the compound represented by the formula II, wherein $R^5$ is Et.

$^1H$ NMR (400 MHz, $CDCl_3$): δ=7.25-6.88 (m, 16H), 3.62 (m, 1H), 2.93 (m, 1H), 2.67 (m, 1H), 1.77 (m, 2H), 1.04 (m, 3H).

Preparation Example 6

Preparation example 6 was used to prepare a halogen-containing compound $I^6$.

In this preparation example, the halogen-containing compound was prepared by the same method as in the preparation example 1, except that tert-butyl ethylene glycol was replaced with methyl ethylene glycol. The prepared compound was subjected to nuclear magnetic resonance analysis, and it may be determined that the prepared compound was the compound represented by the formula II, wherein $R^5$ is Me.

$^1H$ NMR (400 MHz, $CDCl_3$): δ=7.30-6.92 (m, 16H), 3.70 (m, 1H), 2.96 (m, 1H), 2.65 (m, 1H), 1.09 (m, 3H).

Preparation Example 7

Preparation example 7 was used to prepare a halogen-containing compound $I^7$.

In this preparation example, the halogen-containing compound was prepared by the same method as in the preparation example 1, except that difluorophenyl phosphine chloride was replaced with dichlorophenyl phosphine chloride. The prepared compound was subjected to nuclear magnetic resonance analysis, and it may be determined that the prepared compound was the compound represented by the formula I, wherein the substituents on the benzene ring are chlorine (that is, in the formula I, $R^1$, $R^2$, $R^3$, and $R^4$ are ortho-substituents and all of them are chlorine), $R^5$ is $^tBu$, and all of $R^6$, $R^7$ and $R^8$ are hydrogen.

$^1H$ NMR (400 MHz, $CDCl_3$): δ=7.30-6.95 (m, 16H), 3.79 (m, 1H), 2.79-2.60 (m, 2H), 1.15 (s, 9H).

Preparation Example 8

Preparation example 8 was used to prepare a halogen-containing compound $I^8$.

In this preparation example, the halogen-containing compound was prepared by the same method as in the preparation example 1, except that tert-butyl ethylene glycol was replaced with 1-cyclohexyl-2-tert-butyl ethylene glycol. The prepared compound was subjected to nuclear magnetic resonance analysis, and it may be determined that the prepared compound was the compound represented by the formula I, wherein $R^1$, $R^2$, $R^3$ and $R^4$ are ortho-substituents and all of them are fluorine, $R^5$ is $^tBu$, $R^6$ is Cy, and both $R^7$ and $R^8$ are hydrogen.

$^1H$ NMR (400 MHz, $CDCl_3$): δ=7.30-6.90 (m, 16H), 3.60-3.50 (m, 2H), 2.93 (m, 1H), 1.53-1.26 (m, 11H), 1.20 (s, 9H).

Example 1-18 are used to illustrate the present invention.

Example 1

A 300 mL stainless steel polymerization autoclave was heated to 80° C., and vacuumized, then replacement was performed with nitrogen, and subsequently ethylene was filled for replacement. Then, the temperature in the autoclave was lowered to 40° C. Methylcyclohexane (purchased from J&K chemicals, Beijing), 0.5 μmol chromium acetylacetonate (purchased from J&K chemicals, Beijing), and the halogen-containing compound $I^1$ as a ligand (i.e., in the formula II, $R^5$ is $^tBu$), and modified methylaluminoxane (MMAO, purchased from Akzo Nobel) as a co-catalyst were added into the autoclave, and mixed evenly, wherein the total volume of the mixed solution was 100 mL, and the molar ratio of chromium acetylacetonate to the halogen-containing compound to the co-catalyst was 1:2:400, that is, the addition amount of the halogen-containing compound $I^1$ was 1 μmol, and the addition amount of MMAO was 200 μmol. Ethylene was introduced, the pressure of ethylene was controlled to be 3 MPa, and ethylene oligomerization was carried out at a temperature of 40° C. After 30 minutes, 1 mL of ethanol was added as a terminator to terminate the reaction. The temperature in the autoclave was lowered to room temperature (25° C.), and the gas phase products were collected into a gas measuring tank, and the liquid phase products were collected into an erlenmeyer flask. The gas and liquid products were measured respectively and analyzed by gas chromatography to calculate the catalyst activity and the product composition, and the results were listed in Table 1.

Example 2

The ethylene oligomerization was carried out by using the same method as in Example 1, except that the halogen-containing compound as the ligand was replaced with the halogen-containing compound $I^2$ (i.e., in the formula II, $R^5$ is Cy), and the experimental results were listed in Table 1.

Example 3

The ethylene oligomerization was carried out by using the same method as in Example 1, except that the halogen-containing compound as the ligand was replaced with the halogen-containing compound $I^3$ (i.e., in the formula II, $R^5$ is Ph), and the experimental results were listed in Table 1.

Example 4

The ethylene oligomerization was carried out by using the same method as in Example 1, except that the halogen-containing compound as the ligand was replaced with the halogen-containing compound $I^4$ (i.e., in the formula II, $R^5$ is $^iPr$), and the experimental results were listed in Table 1.

Example 5

The ethylene oligomerization was carried out by using the same method as in Example 1, except that the halogen-containing compound as the ligand was replaced with the halogen-containing compound $I^5$ (i.e., in the formula II, $R^5$ is Et), and the experimental results were listed in Table 1.

Example 6

The ethylene oligomerization was carried out by using the same method as in Example 1, except that modified methylaluminoxane as the co-catalyst was replaced with triethylaluminum (purchased from J&K chemicals, Beijing). The experimental results are shown in the Listed in Table 1.

Example 7

The ethylene oligomerization was carried out by using the same method as in Example 1, except that chromium acetylacetonate was replaced with tris(tetrahydrofuran) chromium trichloride (purchased from J&K chemicals, Beijing). The experimental results were listed in Table 1.

Example 8

The ethylene oligomerization was carried out by using the same method as in Example 1, except that the ethylene oligomerization was performed at a temperature of 50° C. The experimental results were listed in Table 1.

Example 9

The ethylene oligomerization was carried out by using the same method as in Example 1, except that the ethylene oligomerization was performed at a temperature of 60° C. The experimental results were listed in Table 1.

Example 10

The ethylene oligomerization was carried out by using the same method as in Example 1, except that the ethylene oligomerization was performed at a temperature of 70° C. The experimental results were listed in Table 1.

Example 11

The ethylene oligomerization was carried out by using the same method as in Example 1, except that the ethylene oligomerization was performed at a temperature of 90° C. The experimental results were listed in Table 1.

Example 12

The ethylene oligomerization was carried out by using the same method as in Example 1, except that the ethylene oligomerization was performed at a temperature of 30° C. The experimental results were listed in Table 1.

Example 13

The ethylene oligomerization was carried out by using the same method as in Example 1, except that the reaction pressure was controlled to be 5 MPa, and the experimental results were listed in Table 1.

Example 14

The ethylene oligomerization was carried out by using the same method as in Example 1, except that the halogen-containing compound as the ligand was replaced with the halogen-containing compound $I^6$ (i.e., in the formula II, $R^5$ is Me). The experimental results were listed in Table 1.

Example 15

The ethylene oligomerization was carried out by using the same method as in Example 1, except that the halogen-containing compound as the ligand was replaced with the halogen-containing compound $I^7$ (i.e., in the formula I, $R^1$, $R^2$, $R^3$, and $R^4$ are ortho-substituents and all of them are chlorine, $R^5$ is $^tBu$, and all of $R^6$, $R^7$ and $R^8$ are hydrogen), and the experimental results were listed in Table 1.

Comparative Example 1

The ethylene oligomerization was carried out by using the same method as in Example 1, except that the halogen-containing compound was replaced with $(S,S)$-$(phenyl)_2$PCH(Me)CH(Me)P$(phenyl)_2$ (marked as D1), and the experimental results were listed in Table 1.

Comparative Example 2

The ethylene oligomerization was carried out by using the same method as in Example 1, except that the halogen-containing compound was replaced with $(S,S)$-$(o$-fluoro-phenyl$)_2$PCH(Me)CH(Me)P$(o$-fluoro-phenyl$)_2$ (marked as D2), and the experimental results were listed in Table 1.

Comparative Example 3

The ethylene oligomerization was carried out by using the same method as in Example 1, except that the halogen-containing compound was replaced with

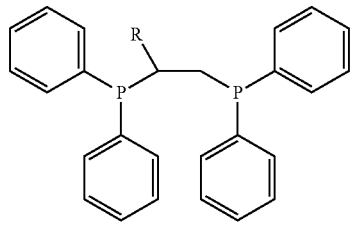

(wherein, R is $^tBu$, marked as D3), and the experimental results were listed in Table 1.

Comparative Example 4

The ethylene oligomerization was carried out by using the same method as in Example 1, except that the halogen-containing compound was replaced with

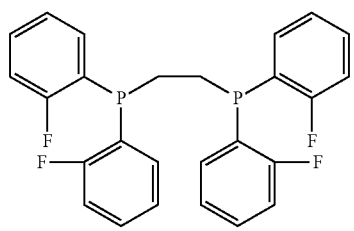 [SMILES: Fc1ccccc1P(CCP(c1ccccc1F)c1ccccc1F)c1ccccc1F]

(marked as D4), and the experimental results were listed in Table 1.

Example 16

A 300 mL stainless steel polymerization autoclave was heated to 80° C., and vacuumized, then replacement was performed with nitrogen, and subsequently ethylene was filled for replacement. Then, the temperature in the autoclave was lowered to 50° C. Heptane (purchased from J&K chemicals, Beijing), 0.5 µmol chromium acetylacetonate, the halogen-containing compound $I^2$ as a ligand (i.e., in the formula II, $R^5$ is Cy), and modified methylaluminoxane (MMAO, purchased from Akzo Nobel) as a co-catalyst were added into the autoclave, and mixed uniformly, wherein the total volume of the mixed solution was 100 mL, and the molar ratio of chromium acetylacetonate to the halogen-containing compound to the co-catalyst is 1:2:500. That is, the addition amount of the halogen-containing compound $I^2$ was 1 µmol, and the addition amount of MMAO was 250 µmol. Ethylene was introduced, the pressure of ethylene was controlled to be 4 MPa, and the ethylene oligomerization was carried out at a temperature of 50° C. After 60 minutes, 1 mL of ethanol was added as a terminator to terminate the reaction. The temperature in the autoclave was lowered to room temperature (25° C.). The gas phase products were collected in a gas measuring tank, and the liquid phase products were collected in an erlenmeyer flask, and the gas and liquid products were measured separately and analyzed by gas chromatography to calculate the catalyst activity and the product composition, and the results were listed in Table 1.

Example 17

A 300 mL stainless steel polymerization autoclave was heated to 80° C., and vacuumized, then replacement was performed with nitrogen, and subsequently ethylene was filled for replacement. Toluene (purchased from J&K chemicals, Beijing), 1.0 mol chromium acetylacetonate, the halogen-containing compound $I^1$ as a ligand (i.e., in the formula II, $R^5$ is $^tBu$), and methylaluminoxane (MAO, purchased from Akzo Nobel) as a co-catalyst were added into the autoclave, and mixed uniformly, wherein the total volume of the mixed solution was 100 mL, and the molar ratio of chromium acetylacetonate to the halogen-containing compound to the co-catalyst was 1:1.5:300, that is, the addition amount of the halogen-containing compound $I^1$ is 1.5 µmol, and the addition amount of MAO is 300 µmol. Ethylene was introduced, the pressure of ethylene was controlled to 2 MPa, and the ethylene oligomerization was carried out at a temperature of 80° C. After 30 minutes, 1 mL of ethanol was added as a terminator to terminate the reaction. The temperature in the autoclave was lowered to room temperature (25° C.). The gas phase products were collected in a gas measuring tank, the liquid phase products were collected in an erlenmeyer flask, and the gas and liquid products were measured separately and analyzed by gas chromatography to calculate the catalyst activity and the product composition, and the results were listed in Table 1.

Comparative Example 5

The ethylene oligomerization was carried out by the same method as in Example 17, except that the halogen-containing compound was replaced with $(S,S)$-$(o$-fluoro-phenyl$)_2$ PCH(Me)CH(Me)P(o-fluoro-phenyl)$_2$ (marked as D2), and the experimental results were listed in Table 1.

Example 18

The ethylene oligomerization was carried out by the same method as in Example 1, except that the halogen-containing compound was replaced with the halogen-containing compound I$^8$ (that is, in the formula I, R$^1$, R$^2$, R$^3$, and R$^4$ are ortho-substituents and all of them are fluorine, R$^5$ is $^t$Bu, R$^6$ is Cy, and both R$^7$ and R$^8$ are hydrogen), and the experimental results were listed in Table 1.

| Groups | Composition of the catalyst (molar ratio) | Activity 10$^8$ g·mol (Cr)$^{-1}$·h$^{-1}$ | C6 selectivity wt % | Content of 1-hexene in C6 % | C8 selectivity wt % | Content of 1-octene in C8 % | Total selectivity of 1-hexene and 1-octene wt % |
|---|---|---|---|---|---|---|---|
| Example 1 | I$^1$/Cr(acac)$_3$/MMAO = 2/1/400 | 2.31 | 34.7 | 97.6 | 61.8 | 99.8 | 95.5 |
| Example 2 | I$^2$/Cr(acac)$_3$/MMAO = 2/1/400 | 2.50 | 31.4 | 97.9 | 64.4 | 99.5 | 94.8 |
| Example 3 | I$^3$/Cr(acac)$_3$/MMAO = 2/1/400 | 2.04 | 36.0 | 97.7 | 60.0 | 99.9 | 95.1 |
| Example 4 | I$^4$/Cr(acac)$_3$/MMAO = 2/1/400 | 1.76 | 37.3 | 97.8 | 58.5 | 99.6 | 94.7 |
| Example 5 | I$^5$/Cr(acac)$_3$/MMAO = 2/1/400 | 1.46 | 35.5 | 97.9 | 60.2 | 99.5 | 94.7 |
| Example 6 | I$^1$/Cr(acac)$_3$/AlEt$_3$ = 2/1/400 | 0.95 | 44.1 | 98.2 | 52.3 | 99.4 | 95.3 |
| Example 7 | I$^1$/CrCl$_3$(THF)$_3$/MMAO = 2/1/400 | 1.55 | 35.0 | 97.5 | 61.1 | 99.7 | 95.0 |
| Example 8 | I$^4$'/Cr(acac)$_3$/MMAO = 2/1/400 | 2.40 | 40.8 | 97.3 | 55.1 | 99.9 | 94.7 |
| Example 9 | I$^4$/Cr(acac)$_3$/MMAO = 2/1/400 | 2.03 | 59.3 | 97.7 | 37.9 | 99.6 | 95.7 |
| Example 10 | I$^4$/Cr(acac)$_3$/MMAO = 2/1/400 | 1.94 | 67.4 | 97.4 | 31.0 | 99.6 | 96.5 |
| Example 11 | I$^4$/Cr(acac)$_3$/MMAO = 2/1/400 | 2.47 | 79.6 | 98.4 | 17.7 | 98.9 | 95.8 |
| Example 12 | I$^4$/Cr(acac)$_3$/MMAO = 2/1/400 | 1.60 | 21.6 | 96.9 | 72.3 | 99.8 | 93.1 |
| Example 13 | I$^4$/Cr(acac)$_3$/MMAO = 2/1/400 | 4.11 | 35.9 | 97.8 | 60.0 | 100 | 95.1 |
| Example 14 | I$^6$/Cr(acac)$_3$/MMAO = 2/1/400 | 1.51 | 32.8 | 97.5 | 62.6 | 99.8 | 94.5 |
| Example 15 | I$^7$/Cr(acac)$_3$/MMAO = 2/1/400 | 1.21 | 33.2 | 98.0 | 62.0 | 99.7 | 94.3 |
| Comparative example 1 | D1/Cr(acac)$_3$/MMAO = 2/1/400 | 0.02 | 25.3 | 73.4 | 43.3 | 97.5 | 60.7 |
| Comparative example 2 | D2/Cr(acac)$_3$/MMAO = 2/1/400 | 0.05 | 41.0 | 98.3 | 50.0 | 99.5 | 90.1 |
| Comparative example 3 | D3/Cr(acac)$_3$/MMAO = 2/1/400 | 0.57 | 25.2 | 75.8 | 54.4 | 99.4 | 73.2 |
| Comparative example 4 | D4/Cr(acac)$_3$/MMAO = 2/1/400 | 0.09 | 24.6 | 96.9 | 42.9 | 98.1 | 65.9 |
| Example 16 | I$^2$/Cr(acac)$_3$/MMAO = 2/1/500 | 3.29 | 39.5 | 98.0 | 56.2 | 99.9 | 94.9 |
| Example 17 | I$^1$/Cr(acac)$_3$/MAO = 1.5/1/300 | 1.01 | 72.1 | 98.3 | 22.0 | 99.0 | 92.7 |
| Comparative example 5 | D$^2$/Cr(acac)$_3$/MAO = 1.5/1/300 | 0.04 | 42.3 | 96.8 | 49.1 | 99.5 | 89.8 |
| Example 18 | I$^8$/Cr(acac)$_3$/MMAO = 2/1/400 | 0.80 | 40.1 | 98.0 | 53.0 | 99.6 | 92.1 |

As seen from the data in Table 1, the catalyst composition according to the present invention has outstanding performance in ethylene oligomerization, with a catalytic activity of 0.8×10$^8$ g·mol(Cr)$^{-1}$·h$^{-1}$ or above, up to 4×10$^8$ g·mol (Cr)$^{-1}$·h$^{-1}$ or above, and the total selectivity of 1-hexene and 1-octene is 92 wt % or above, and up to above 95 wt %, under different conditions. The data in Table 1 indicates that the change in the structure of the catalyst ligand has a significant effect on the improvement of catalytic performance. Compared with the comparative examples 1-4, the catalyst composition according to the present invention has a significantly improved catalyst activity, which may generate a good balance between the catalytic activity and the product selectivity, decrease the production of by-products such as cycloolefins and cyclized products, demonstrating that the halogen-containing compound of the present invention has better performance as a ligand.

In addition, during the polymerization reaction, the catalytic system of the catalyst composition according to the present invention initiates quickly and runs smoothly, and can more effectively catalyze the trimerization and tetramerization of ethylene. Wherein, the catalyst composition according to the present invention can maximize ethylene absorption in just a few minutes (within 5 minutes) for half an hour or above. This shows that the catalyst composition according to the present invention has high practicability and broad prospects for industrialization.

The preferred embodiments of the present invention have been described in detail above, but the present invention is not limited thereto. A variety of simple variations can be made to the technical solutions of the present invention within the scope of the technical concept of the present invention, including combinations of individual technical features in any other suitable manner, and these simple variations and combinations should also be regarded as the disclosure of the present invention and within the scope of protection of the present invention.

The invention claimed is:

1. A halogen-containing compound represented by Formula II:

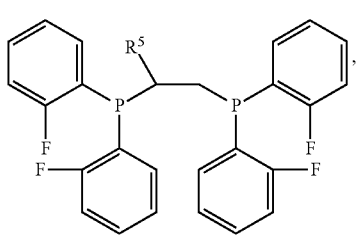

Formula II wherein R$^5$ is selected from the group consisting of C$_1$-C$_{12}$ alkyl, C$_3$-C$_{12}$ cycloalkyl, C$_6$-C$_{20}$ aryl, C$_1$-C$_8$ alkyl, C$_3$-C$_8$ cycloalkyl, C$_6$-C$_{16}$ aryl, C$_1$-C$_6$ alkyl, C$_3$-C$_6$ cycloalkyl, C$_6$-C$_{12}$ aryl, methyl, ethyl, n-propyl, isopropyl, n-butyl, tert-butyl, isobutyl, n-pentyl, isopentyl, tert-pentyl, cyclopropyl, cyclobutyl, cyclopentyl, cyclohexyl, phenyl, methylphenyl, ethylphenyl, chlorophenyl, naphthyl, tert-butyl, cyclohexyl, phenyl, isopropyl, ethyl, tert-butyl, cyclohexyl, and phenyl.

2. An ethylene oligomerization catalyst composition, comprising the halogen-containing compound according to claim 1, a transition metal compound, and a co-catalyst.

3. The composition according to claim 2, wherein a molar ratio of the halogen-containing compound to the transition metal compound is 1:0.1-10 and a molar ratio of the halogen-containing compound to the co-catalyst is 1:1-1000.

4. The composition according to claim 2, wherein the transition metal compound is at least one selected from the group consisting of a chromium compound, a molybdenum compound, an iron compound, a titanium compound, a zirconium compound, a nickel compound, chromium acetylacetonate, chromium isooctanoate, tris(tetrahydrofuran) chromium trichloride, and bis(tetrahydrofuran) chromium dichloride, and
wherein the co-catalyst is at least one selected from the group consisting of an aluminum-containing co-catalyst, an organoaluminum compound alkyl aluminum, alkoxy aluminum, alkyl aluminum halide, methylaluminoxane, trimethylaluminum, triethylaluminum, triisobutylaluminum, tri-n-hexylaluminum, tri-n-octylaluminum, aluminium diethyl monochloride, aluminium ethyl dichloride, ethylaluminoxane, modified methylaluminoxane, modified methylaluminoxane, methylaluminoxane, and triethylaluminum.

5. An ethylene oligomerization method, comprising a step of contacting ethylene with the catalyst composition according to claim 2.

6. The method according to claim 5, wherein the contacting is carried out in an organic solvent selected from the group consisting of $C_6$-$C_{12}$ alkane, $C_6$-$C_{12}$ cycloalkane, $C_6$-$C_{12}$ aromatic hydrocarbon, and mixtures thereof; or,
the organic solvent is selected from the group consisting of methylcyclohexane, heptane, cyclohexane, toluene, xylene, and mixtures thereof; or,
the organic solvent is used in an amount such that a concentration of the catalyst composition, in terms of a transition metal element in the transition metal compound, is 1-20 μmol/L.

7. The method according to claim 5, wherein the contacting is carried out at a temperature of 0-200° C., and under a pressure of ethylene is 0.1-20 MPa.

8. An ethylene trimerization method, comprising a step of contacting ethylene with the catalyst composition according to claim 2 at a temperature of 60° C. or above.

9. The ethylene trimerization method according to claim 8, wherein the contacting is carried out in at least one organic solvent selected from the group consisting of $C_6$-$C_{12}$ alkane, $C_6$-$C_{12}$ cycloalkane, $C_6$-$C_{12}$ aromatic hydrocarbon, and mixtures thereof; or,
the organic solvent is selected from the group consisting of methylcyclohexane, heptane, cyclohexane, toluene, xylene, and mixtures thereof; or,
the organic solvent is used in an amount such that concentration of the catalyst composition, in terms of a transition metal element in the transition metal compound, is 1-20 μmol/L.

10. The ethylene trimerization method according to claim 8, wherein the pressure of ethylene is 0.1-20 MPa.

11. The ethylene trimerization method according to claim 8, wherein the contacting is carried out at a temperature of 60-90° C.

12. An ethylene tetramerization method, comprising a step of contacting ethylene with the catalyst composition according to claim 2 at a temperature of lower than 60° C.

13. The ethylene tetramerization method according to claim 12, wherein the contacting is carried out in an organic solvent selected from the group consisting of $C_6$-$C_{12}$ alkane, $C_6$-$C_{12}$ cycloalkane, $C_6$-$C_{12}$ aromatic hydrocarbon, and mixtures thereof; or,
the organic solvent is selected from methylcyclohexane, heptane, cyclohexane, toluene, xylene, and mixtures thereof; or,
the organic solvent is used in an amount such that a concentration of the catalyst composition, in terms of a transition metal element in the transition metal compound, is 1-20 μmol/L.

14. The ethylene tetramerization method according to claim 12, wherein the pressure of ethylene is 0.1-20 MPa.

15. The ethylene tetramerization method according to claim 12, wherein the contacting is carried out at a temperature of 30-50° C.

* * * * *